(12) United States Patent
Bhak et al.

(10) Patent No.: US 9,208,283 B2
(45) Date of Patent: Dec. 8, 2015

(54) GROUPING SYSTEM USING GENOTYPE-BASED SNS

(71) Applicant: GENOME RESEARCH FOUNDATION, Gyeonggi-do (KR)

(72) Inventors: Jong Hwa Bhak, Gyeongsangnam-do (KR); Chang Uk Kim, Gyeonggi-do (KR); Sung Hoon Lee, Daejeon (KR); Su An Cho, Gyeonggi-do (KR)

(73) Assignee: GENOME RESEARCH FOUNDATION, Gyeonggi-do (KR)

( * ) Notice: Subject to any disclaimer, the term of this patent is extended or adjusted under 35 U.S.C. 154(b) by 206 days.

(21) Appl. No.: 14/147,120

(22) Filed: Jan. 3, 2014

(65) Prior Publication Data

US 2014/0207780 A1    Jul. 24, 2014

(51) Int. Cl.
| | | |
|---|---|---|
| *G06F 7/00* | (2006.01) |
| *G06F 19/28* | (2011.01) |
| *C12N 15/82* | (2006.01) |
| *G06F 19/18* | (2011.01) |

(52) U.S. Cl.
CPC ............ *G06F 19/28* (2013.01); *C12N 15/8286* (2013.01); *G06F 19/18* (2013.01)

(58) Field of Classification Search
CPC ........... C12N 15/8286; C12N 15/8245; C12N 15/8251; C12N 15/8274; C12N 15/8289
See application file for complete search history.

*Primary Examiner* — Truong Vo
(74) *Attorney, Agent, or Firm* — Rabin & Berdo, P.C.

(57) ABSTRACT

Disclosed is a grouping system using a genotype-based SNS in that, when the peoples having a genotype want to form their community, it provides a means of access to the genotype of an individual's particular position within the limit of a technical security maintenance, so that the social networks is constituted online according to the genetic identity, whereby satisfying personal tastes of the members.

4 Claims, 4 Drawing Sheets

| Group name | To our brighter and faster future |
|---|---|
| Group condition | chr1 1234 = AT and chr2 789 = GG |
| Group information | Genetic trait having a high risk of becoming bald-headed before the thirties. |

FIG. 4

GROUPING SYSTEM USING GENOTYPE-BASED SNS

BACKGROUND OF THE INVENTION

1. Field of the Invention

The present invention relates to a grouping system using a genotype-based SNS. More particularly, the present invention relates to a grouping system using a genotype-based SNS in that, when the peoples having a genotype want to form their community, it provides a means of access to the genotype of an individual's particular position within the limit of a technical security maintenance, so that the social networks is constituted online according to the genetic identity, whereby satisfying personal tastes of the members.

2. Description of the Prior Art

All living things including humans have any characteristic of multiplying the individuals similar to themselves. It is called as a "genetic phenomenon". This genetic phenomenon is achieved by the genetic material named as a DNA, which is contained in the nucleus of a cell.

In this way, the human preserves and evolves it won species by means of the genetic phenomenon. Also, all the biological and sociological activities such as a birth and a growth process of each individual, a disease, a death etc. are closely related to the expression of this gene. A series of these biological and sociological phenomena are stored in various genes as encoded genetic information.

The gene is a genetic information necessary to make the protein, which is the most important component of the biological phenomenon. It is represented as a base sequence of the DNA named as arginine (A), thiamine (T), guanine (G), cytosine (C).

The consecutive three base sequences in the DNA referred to a Codon (C) is transcribed into an RNA and then, is translated into a particular amino acid. Then, the proteins combined by various amino acids are created and these proteins form the main structure in the cell and mediate the reactions of determining the fate of human beings through the role of a hormone and an enzyme etc.

The genome of synthesizing the gene and the chromosome is an assembly of all genetic information (DNA) contained in one organism. This genome information has any information capable of determining the outward appearance (phenotype) of each individual in the gravitational field and the given time space named as an earth.

On the other hand, each individual with similar genomic information is likely to be similar externally.

The human genome, it is now known, is composed of a pair of about 3 billion DNA base sequences. According to the genome project, it is known that the number of the genes of representing specific functions is about 30,000-40,000.

Even in the case of the gene illustrating the same genetic traits (for example, race or blood type etc.), the base sequences thereof differ from individual to individual. The specific gene fragments of this individual are called as an allele.

Even it shares the same genes, the genetic elements of each individual are different from each other. Accordingly, a single nucleotide polymorphism (SNP) makes all of the differences of each individual. The concept of the single nucleotide polymorphism (SNP) is the most important element in the personal recognition and identification. The genetic and biological properties of each individual can be seen due to the difference of the single nucleotide polymorphism (SNP).

These genetic elements are also associated with the diseases of all humans. The disease resistance, the disease sensitivity, and the degree of the disease may vary depending on the difference of the SNP in each individual.

On the other hand, according to the recent development of the Internet, an interest in a social network service (SNS) showing social relations based on the relations between I, my friends and friends of my friends has greatly increased.

In Korea, the Cyworld (www.cyworld.com) provides a simple relationship service of finding the relationship between the subscribers on the basis of the first degree relationship configured by the subscribers and provides the social network service by attracting a large number of subscribers all over the world.

In these conventional social network services, the list (friends list) of the peoples who are acquainted with himself is filled in the joined service and it forms the personal connections thereof.

However, there is a problem in that the conventional social network forming method can provide only the connection management of a simple form using general information such as his area, his education, his hobby, his symbol and so on.

Also, there is another problem in that the conventional social network forming method cannot grasp the genetic relationship between members.

Especially, even in the community club, since it is difficult to verify the members, who cannot be identified with him, anyone is eligible to join. Also, it is difficult to form the community between the members having homogeneity in terms of the biological activity, the hobby, and the tendency and so on.

SUMMARY OF THE INVENTION

Accordingly, the present invention has been made to solve the above-mentioned problems occurring in the prior art, and an object of the present invention is to provide a grouping system using a genotype-based SNS in that, when the peoples having a genotype want to form their community, it provides a means of access to the genotype of an individual's particular position within the limit of a technical security maintenance, so that the social networks is constituted online according to the genetic identity, whereby satisfying personal tastes of the members.

In order to accomplish this object, there is provided a grouping system using a genotype-based SNS, including: a membership terminal 200 for providing detail information and genome information of the member to a genotype grouping server and setting SNS join groups and disclosure or non-disclosure thereof during group join; and the genotype grouping server 100 comprising: a membership information acquiring unit 110 for acquiring the detail information and genome information of the member provided from the membership terminal 200; an information storing and managing unit 120 for storing the genome information acquired by the membership information acquiring unit 110 in a genome information DB 130 and storing the detail information in a membership detail information DB 140; the genome information DB 130 for storing the genome information of the member; the membership detail information DB 140 for storing the detail information of the member; a genotype group generating unit 150 for acquiring the group name, the genotype condition, and the attribute of an expression information set by the specific membership terminal, which is desired to generate the group, so as to generate a genotype group; a join setting information acquiring unit 160 for acquiring any one of the group name, the genotype condition, and the expression information of the SNS join group set from the membership terminal 200; a genotype group join allowing unit 170 for extracting information acquired by the join setting information acquiring unit 160 and the corresponding membership information stored in the membership detail information DB 140 and then, extracting the genotype information of the genome information of the corresponding member from the genome information DB 130 so as to allow the group join when the genotype condition generated by the genotype group generating unit 150 is identical with the extracted genotype information; and a disclosure type storing and managing unit 180 for acquiring the disclosure or the nondisclosure set from the membership terminal 200 so as to store and manage the location information of the chromosomes and the information on the disclosure allowance, the conditional disclosure, and the nondisclosure about the corresponding location information thereof.

Preferably, the membership terminal 200 includes: a membership information providing unit 210 for providing the detail information and the genome information of the member to the genotype grouping server; a join group setting unit 220 for setting the SNS join group among the groups provided by the genotype grouping server 100; and a disclosure condition setting unit 230 for setting the information on the disclosure allowance, the conditional disclosure, and the nondisclosure about the location information of the chromosomes and the corresponding location information thereof.

Preferably, the expression information is a phenotype information corresponding to the genotype condition.

Preferably, a condition of the group generated by the genotype group generating unit 150 provides a combination of multiple conditions using an "and" operator or an "or" operator.

BRIEF DESCRIPTION OF THE DRAWINGS

The above and other objects, features and advantages of the present invention will be more apparent from the following detailed description taken in conjunction with the accompanying drawings, in which:

FIG. 4 is an exampling view illustrating an example of a table of defining an attribute of a group of a grouping system using a genotype-based SNS according to one embodiment of the present invention.

DETAILED DESCRIPTION OF THE PREFERRED EMBODIMENTS

Hereinafter, an exemplary embodiment of the present invention will be described in detail with reference to the accompanying drawings.

Figure 1:
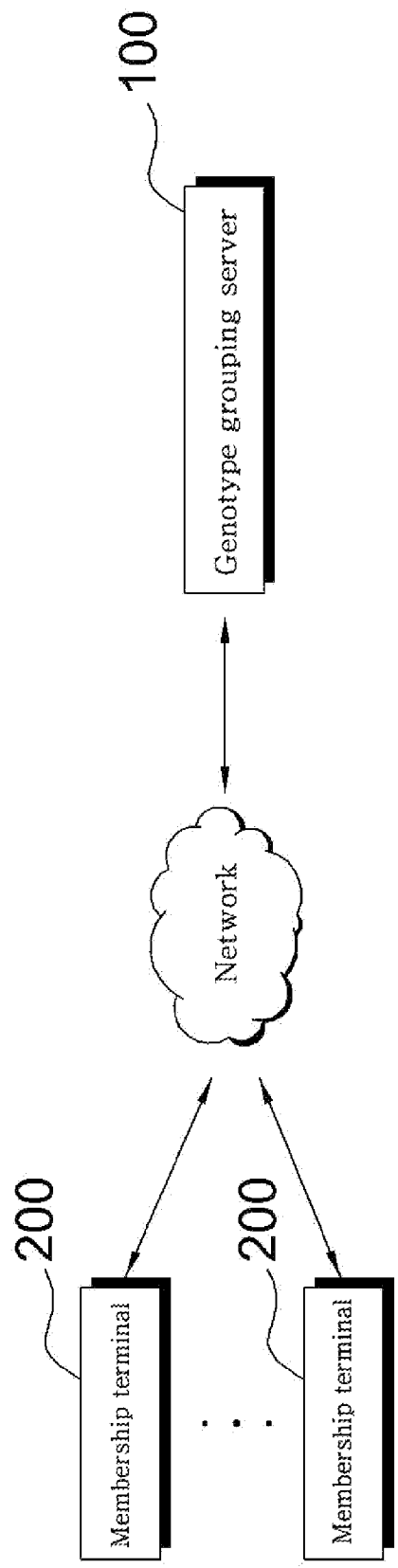
FIG. 1 is an entire block diagram illustrating a grouping system using a genotype-based SNS according to one embodiment of the present invention.

FIG. 1 is an entire block diagram illustrating a grouping system using a genotype-based SNS according to one embodiment of the present invention.

As shown in FIG. 1, the grouping system using a genotype-based SNS according to one embodiment of the present invention includes:

a membership terminal 200 for providing detail information and genome information of the member to a genotype grouping server 100 and setting SNS join groups and disclosure or non-disclosure thereof during group join; and the genotype grouping server 100 for acquiring a group name, a genotype condition, and an attribute of a phenotype information set by a specific membership terminal, which is desired to generate the group, so as to generate a genotype group; acquiring any one of a group name, a genotype condition, and a phenotype information of a SNS join group set from the membership terminal 200 so as to allow the group join when the genotype condition for the group join is identical with the genotype information provided by the membership terminal 200; and acquiring the disclosure or the non-disclosure set from the membership terminal 200 so as to store and manage location information of chromosomes and information on a disclosure allowance, a conditional disclosure, and the nondisclosure about the corresponding location information thereof.

Specifically, the genome information is generally the result value analyzed by the genetic information analyzing apparatus. Since the genetic information analysis method and the analysis apparatus and technique thereof for analyzing the genetic information of individuals produced through a SNP chip and a genome sequencing are widely known in the art, the detailed descriptions on those are omitted here.

Figure 2:
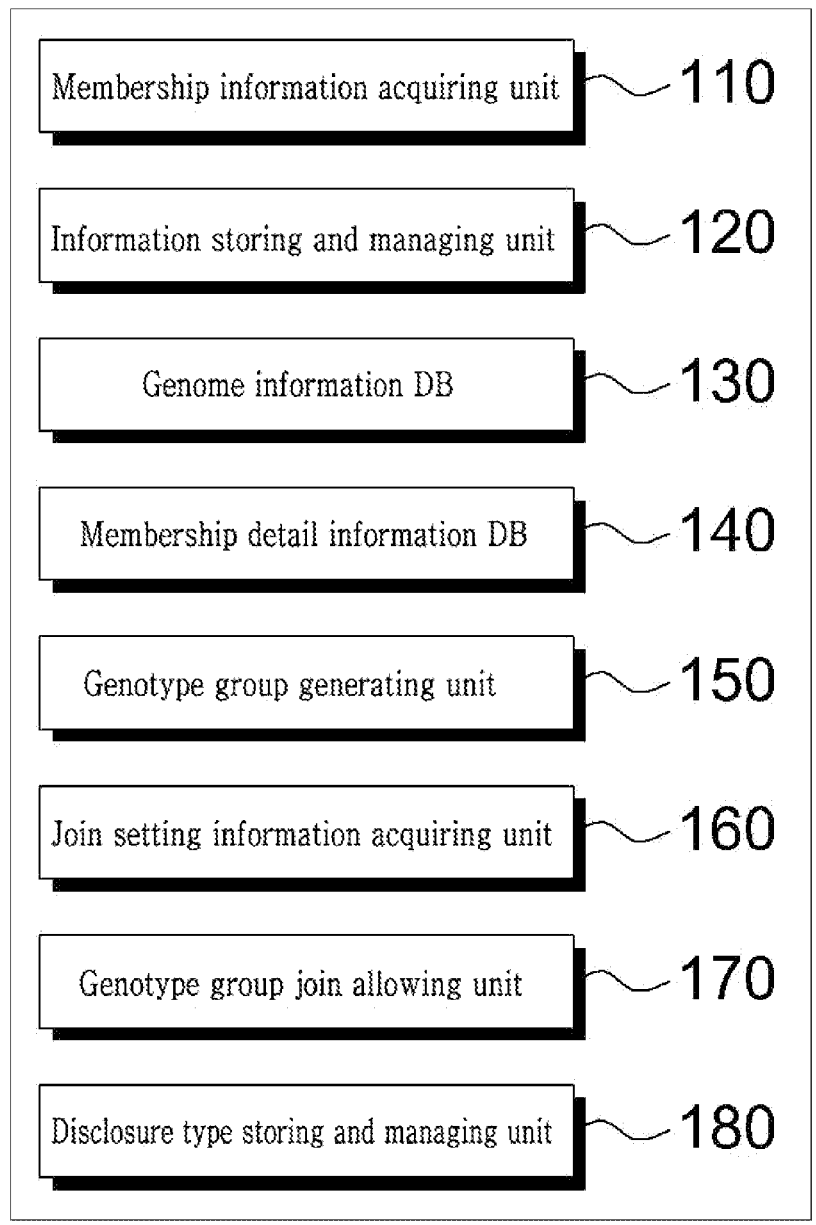
FIG. 2 is a block diagram illustrating a genotype grouping server of a grouping system using a genotype-based SNS according to one embodiment of the present invention.

FIG. 2 is a block diagram illustrating a genotype grouping server of a grouping system using a genotype-based SNS according to one embodiment of the present invention.

As shown in FIG. 2, the genotype grouping server 100 of the grouping system using the genotype-based SNS according to one embodiment of the present invention includes:

a membership information acquiring unit 110 for acquiring the detail information and genome information of the member provided from the membership terminal 200;

an information storing and managing unit 120 for storing the genome information acquired by the membership information acquiring unit 110 in a genome information DB 130 and storing the detail information in a membership detail information DB 140;

the genome information DB 130 for storing the genome information of the members;

the membership detail information DB 140 for storing the detail information of the members;

a genotype group generating unit 150 for acquiring the group name, the genotype condition, and the attribute of the phenotype information set by the specific membership terminal, which is desired to generate the group, so as to generate a genotype group;

a join setting information acquiring unit 160 for acquiring any one of the group name, the genotype condition, and the phenotype information of the SNS join group set from the membership terminal 200;

a genotype group join allowing unit 170 for extracting information acquired by the join setting information acquiring unit 160 and the corresponding membership information stored in the membership detail information DB 140 and then, extracting the genotype information of the genome information of the corresponding member from the genome information DB 130 so as to allow the group join when the genotype condition generated by the genotype group generating unit 150 is identical with the extracted genotype information; and a disclosure type storing and managing unit 180 for acquiring the disclosure or the nondisclosure set from the membership terminal 200 so as to store and manage the location information of the chromosomes and the information on the disclosure allowance, the conditional disclosure, and the nondisclosure about the corresponding location information thereof.

More concretely, the membership information acquiring unit 110 serves to acquire the detail information and genome information of the member provided from the membership terminal 200.

The detail information includes the member's name, social security number, hobbies, his area, education information, and login ID and password and so on.

The genome information means the chromosome, the position information thereof, and the genotype information.

The information storing and managing unit 120 serves to store the genome information acquired by the membership information acquiring unit 110 in the genome information DB 130 and store the detail information in the membership detail information DB 140.

The genotype group generating unit 150 serves to acquire the group name, the genotype condition, and the attribute of the phenotype information set by the specific membership terminal, which is desired to generate the group, so as to generate the genotype group.

For example, as shown in Table 1, the genotype of any one member is stored together with the chromosome and the location thereof as one set.

TABLE 1

| Chromosome | Location | Genotype |
|---|---|---|
| Chr1 | 1234 | AT |
| Chr2 | 5678 | GC |
| ... | ... | ... |
| ChrM | 123 | AG |

In this case, if one member having the matching set generates a specific group and executes the SNS service, one group is defined as the attributes including the name thereof, the condition (genotype), the information (phenotype) and so on.

That is, as shown in FIG. 4, the group name is "To our brighter and faster future", the group condition is "chr1 1234=AT and chr2 789=GG", and the group information is defined as a genetic trait having a high risk of becoming bald-headed before the thirties.

The group name is any name capable of representing the corresponding group. Also, only the member adequate to the condition of the group (genotype) can be approved to join.

The condition of the group can include a combination of multiple conditions using an operator such as "and" and "or" and so forth.

The group information means the phenotype information corresponding to the genotype defined in the group conditions.

The members can search for groups. In this case, the groups can be searched through general search portal sites. Also, it can search the groups in the homepage site of the corresponding system.

The join setting information acquiring unit 160 serves to acquire any one of the group name, the genotype condition, and the phenotype information of the SNS join group set from the membership terminal 200.

That is, the member searches any one of the group name, the genotype, and the phenotype and requests the group join, so that the member can acquire the group condition set by the corresponding user.

The genotype group join allowing unit 170 serves to extract the information acquired by the join setting information acquiring unit 160 and the corresponding membership information stored in the membership detail information DB 140.

For example, after it acquires the name called as "HONG, Gil-dong", the ID, and the password, it judges as to whether the acquired information is identical with the corresponding membership information or not.

Then, if it is identical with the corresponding membership information, the genotype group join allowing unit 170 extracts the genotype information of the genome information of the corresponding member from the genome information DB 130 so as to allow the group join when the genotype condition generated by the genotype group generating unit 150 is identical with the extracted genotype information.

At this time, the disclosure type storing and managing unit 180 serves to acquire the disclosure or the nondisclosure set from the membership terminal 200 so as to store and manage the location information of the chromosomes and the information on the disclosure allowance, the conditional disclosure, and the nondisclosure about the corresponding location information thereof.

In other words, the disclosure type storing and managing unit 180 servers to limit the content of the service depending on the disclosure or nondisclosure of the detail information (for example, the detail information of the member opens to all members or only the administrator) received from the membership terminal 200.

More specifically, when the information of one member is opened to other members, the information of other members is also opened to the corresponding member.

On the contrary, when the information of one member is not opened to other members, the information of other members is not opened to the corresponding member.

Figure 3:
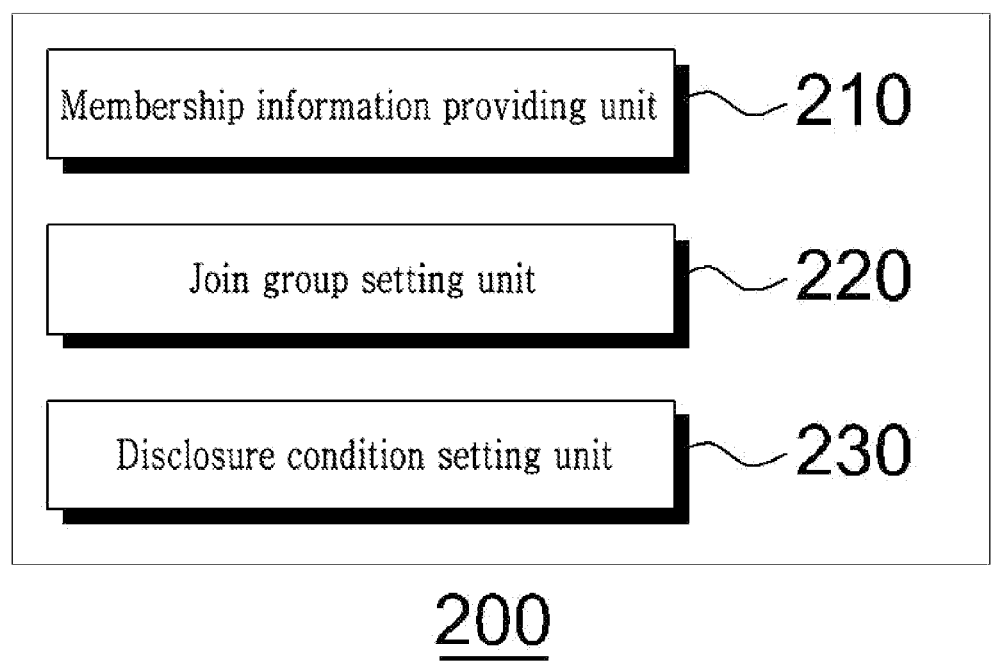
FIG. 3 is a block diagram illustrating a membership terminal of a grouping system using a genotype-based SNS according to one embodiment of the present invention.

FIG. 3 is a block diagram illustrating a membership terminal of a grouping system using a genotype-based SNS according to one embodiment of the present invention.

As shown in FIG. 3, the membership terminal 200 of the grouping system using the genotype-based SNS according to one embodiment of the present invention includes:

a membership information providing unit 210 for providing the detail information and the genome information of the member to the genotype grouping server 100;

a join group setting unit 220 for setting the SNS join group among the groups provided by the genotype grouping server 100; and a disclosure condition setting unit 230 for setting the information on the disclosure allowance, the conditional disclosure, and the nondisclosure about the location information of the chromosomes and the corresponding location information thereof.

That is, the membership information providing unit 210 serves to provide the detail information and the genome information of the member to the genotype grouping server 100.

Also, the join group setting unit 220 serves to set the SNS join group among the groups provided by the genotype grouping server.

Moreover, the disclosure condition setting unit 230 serves to set the information on the disclosure allowance, the conditional disclosure, and the nondisclosure about the location information of the chromosomes and the corresponding location information thereof.

The genotype grouping server 100 acquires the set information and then, the acquired information is stored in the genome information DB 130 and the membership detail information DB 140.

According to the grouping system using the genotype-based SNS of the present invention, when the peoples having a genotype want to form their community, it provides a means of access to the genotype of an individual's particular position within the limit of a technical security maintenance, so that the social networks is constituted online according to the genetic identity, whereby satisfying personal tastes of the members.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A grouping system using a genotype-based SNS, comprising:
    a membership terminal 200 for providing detail information and genome information of the member to a genotype grouping server 100 and setting SNS join groups and disclosure or non-disclosure thereof during group join; and
    the genotype grouping server 100 comprising:
    a membership information acquiring unit 110 for acquiring the detail information and genome information of the member provided from the membership terminal 200;
    an information storing and managing unit 120 for storing the genome information acquired by the membership information acquiring unit 110 in a genome information DB 130 and storing the detail information in a membership detail information DB 140;
    the genome information DB 130 for storing the genome information of the member;
    the membership detail information DB 140 for storing the detail information of the member;
    a genotype group generating unit 150 for acquiring the group name, the genotype condition, and the attribute of an expression information set by the specific membership terminal, which is desired to generate the group, so as to generate a genotype group;
    a join setting information acquiring unit 160 for acquiring any one of the group name, the genotype condition, and the expression information of the SNS join group set from the membership terminal 200;
    a genotype group join allowing unit 170 for extracting information acquired by the join setting information acquiring unit 160 and the corresponding membership information stored in the membership detail information DB 140 and then, extracting the genotype information of the genome information of the corresponding member from the genome information DB 130 so as to allow the group join when the genotype condition generated by the genotype group generating unit 150 is identical with the extracted genotype information; and
    a disclosure type storing and managing unit 180 for acquiring the disclosure or the nondisclosure set from the membership terminal 200 so as to store and manage the location information of the chromosomes and the information on the disclosure allowance, the conditional disclosure, and the nondisclosure about the corresponding location information thereof.

2. A grouping system using a genotype-based SNS, as claimed in claim 1, wherein the membership terminal 200 comprises:
    a membership information providing unit 210 for providing the detail information and the genome information of the member to the genotype grouping server 100;
    a join group setting unit 220 for setting the SNS join group among the groups provided by the genotype grouping server 100; and
    a disclosure condition setting unit 230 for setting the information on the disclosure allowance, the conditional disclosure, and the nondisclosure about the location information of the chromosomes and the corresponding location information thereof.

3. A grouping system using a genotype-based SNS, as claimed in claim 1, wherein the expression information is a phenotype information corresponding to the genotype condition.

4. A grouping system using a genotype-based SNS, as claimed in claim 1, wherein a condition of the group generated by the genotype group generating unit 150 provides a combination of multiple conditions using an "and" operator or an "or" operator.

* * * * *